United States Patent [19]

Wiener et al.

[11] Patent Number: 4,792,625

[45] Date of Patent: Dec. 20, 1988

[54] PROCESS FOR THE REDUCTION OF ORGANIC COMPOUNDS USING ALKALI FORMATE SALTS

[75] Inventors: Harold Wiener, Jerusalem; Shmuel Vandel, Rishon LeZion; Yoel Sasson, Jerusalem, all of Israel

[73] Assignee: Yissum Research Development Company, Jerusalem, Israel

[21] Appl. No.: 71,643

[22] Filed: Jul. 9, 1987

[30] Foreign Application Priority Data

Jul. 31, 1986 [IL] Israel ........................................ 79573

[51] Int. Cl.$^4$ ............................ C07C 5/02; C07C 85/11
[52] U.S. Cl. ................................... 564/416; 564/494; 585/269; 585/277
[58] Field of Search ................ 564/416, 494; 585/269, 585/277

[56] References Cited

FOREIGN PATENT DOCUMENTS 1458633 12/1976 United Kingdom ................ 564/416
1457608 12/1976 United Kingdom ................ 564/416

OTHER PUBLICATIONS

Entwistle et al, J.C.S. Parkin I, pp. 443–444 (1977).
Chemical Abstract 101:6560h (1984).
Chemical Abstract 96:122308j (1981).
Chemical Abstract 87:22732p (1976).
Chemical Abstract 87:5533g (1977).
Chemical Abstract 98:125331p (1982).
Chemical Abstract 98:16244s (1982).
Chemical Abstract 77:74590d (1972).

*Primary Examiner*—Asok Pal
*Attorney, Agent, or Firm*—Felfe & Lynch

[57] ABSTRACT

The invention provides a process for reducing substantially water insoluble organic compounds containing reducible groups comprising contacting these compounds with an aqueous solution of a formic acid salt in the presence of a hydrogenation catalyst and in the substantial absence of a phase transfer catalyst.

10 Claims, No Drawings

PROCESS FOR THE REDUCTION OF ORGANIC COMPOUNDS USING ALKALI FORMATE SALTS

The present invention relates to a process for the reduction of water immisible and sparingly water soluble organic compounds (hereinafter referred to as substantially water insoluble organic compounds).

More particularly, the present invention relates to the reduction of an organic compound containing a reducible group such as a water immiscible or sparingly water soluble aromatic or heteroaromatic compound containing a nitro or azo group, or a water immiscible or sparingly water soluble unsaturated organic compound, comprising contacting said compounds with an aqueous solution of a formic acid salt in the presence of a hydrogenation catalyst and in the substantial absence of a phase transfer catalyst.

The process of the present invention is preferably based on the use of alkali formate salts and hydrogenation agents in a transfer hydrogenation reaction, by the action of a supported Group VIII metal or catalyst.

This three-phase system consists of an aqueous formate salt solution, an organic, substantially water-immiscible, solution containing the substrate whichis to be reduced and a third solid phase of a Group VIII metal supported catalyst, without the need of using a solvent, high temperatures or a phase transfer catalyst.

As is known, reduction of organic compounds is an important process both in the laboratory and in industry. Some important examples of those reactions are: reduction of nitroaromatics to the corresponding amines, hydrogenation of unsaturated compounds, hydrogenolysis of aryl halides, reduction of aldehydes and ketones to alcohols and reduction of azo compounds, etc.

Catalytic hydrogenation using molecular hydrogen is a well-known field as described, e.g. by Rylander, P. N. "Organic Syntheses with Noble Metal Catalysts", Academic Press: London, 1973, pp. 1–74 and Freifelder, M. "Catalytic Hydrogenation in Organic Synthesis", J. Wiley & Sons, USA, 1978. The use, however, of hydrogen gas suffers from several disadvantages. These include high diffusibility, flammability and explosivity of hydrogen gas, necessitating special equipment in order to avoid fire and explosion hazards. In addition, due to its very low density the transportation of hydrogen gas is carried out in high pressure cylinders and costs are often prohibitive.

Far less explored is the field of reduction of organic compounds with the aid of a hydrogen donor molecular in the presence of either a homogeneous or heterogeneous catalyst (as described, e.g., by R. A. W. Johnstone and A. H. Wilby, Chem. Revs. 85, 129–170 (1985)), which process is known as catalytic transfer hydrogenation. Most transfer hydrogenation mechanisms are poorly understood, especially those dealing with heterogeneous catalysts.

A major advantage of the heterogeneous catalyst systems over the homogeneous ones lies in the ease with which the catalyst can be separated after reaction by simple filtration and reused afterwards. For example British Pat. No. 1457608 discloses processes for reducing nitroaromatic water-insoluble compounds by contacting the compounds with an aqueous solution of a formic acid salt in the presence of a heterogeneous hydrogenation catalyst and a surface active agent, particularly a phase transfer catalyst.

British Pat. No. 1458633 also discloses a process for dehalogenating water-immiscible aromatic compounds by contacting the said compound with an aqueous solution of a formic acid salt in the presence of a hydrogenation catalyst and a surface active agent or a phase transfer catalyst.

These patents, however, teach and claim that these processes must be carried out in the presence of a phase transfer catalyst and/or a surface active agent in order to obtain desirable yields.

In said British Patents it is also stressed that two to three folds formate salt equivalent should be used in order to reach high conversions.

German Pat. No. 2536914 discloses a process in which water soluble organic compounds such as nitrosulfonic or carboxylic acid salts are reduced by formate salts in the absence of a surface active agent or a phase transfer catalyst which are unnecessary when only one phase is present. From the above mentioned British patents one can learn that heretofore it was believed and taught that the use of a phase transfer catalyst is essential for reducing water insoluble compounds where two phases are present in contradistinction to said Germany patent from which one would understand that only with water soluble compounds is the use of a phase transfer catalyst not required.

These latter processes, as set forth in said British patents, which represent the latest advance in the art, require temperatures of about 100° C. and give conversion ratios which could be improved upon. Also, as stated before, these processes require the use of a phase transfer catalyst or a surface active agent when water insoluble compounds are to be reduced, making the process troublesome because of the need of separation and recycling of the expensive phase transfer catalyst from the reaction mixture.

While studying those patents one can note that not only is there no preference for any particular formate salt as hydrogen donor; but also they deal exclusively in their examples with sodium formate salt as hydrogen donor, remarking as to the necessity of a two or three fold excess of the formate salt in comparison with the stoichiometric amounts.

It has now been discovered that nitroaromatic and unsaturated water insoluble compounds can be successfully converted to their respective hydrogenated products by contacting an aqueous solution of a formic acid salt with an organic solution of the substrate in the presence of a hydrogenation catalyst, preferably a supported Group VIII metal catalyst on any inactive support, without the use of any phase transfer catalyst or surface active agent. This reaction is performed at mild conditions of temperature and pressure and by using the stoichiometric equivalent amount of formate salt without the need of excess of the hydrogenation agent as shown in Reactions 1a and 1b.

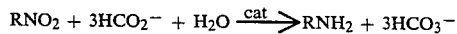

(1a)

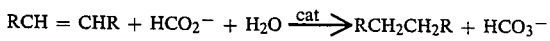

(1b)

The process of the invention can be used for all types of reductions which are normally carried out with hydrogen gas and a catalyst. Thus carbon-carbon, carbon-nitrogen and carbon-oxygen multiple bonds may be reduced.

This process is, however, especially useful for the reduction of water immiscible or sparingly water soluble nitro or azo aromatic and heteroaromatic ring compounds containing a nitro or azo group and for organic compounds containing unsaturated carbon-carbon bonds.

The rings may also contain other substituent groups, for example alkyl, phenyl, phenylalkyl, hydrogen, alkoxy, phenoxy, amino, alkylamino, phenylamino, acylamino, hydroxyalkyl, aminoalkyl, haloalkyl, formyl, a carboxylic ester, cyano, alkyl and arylsulphone among others.

The formic acid salt is an alkali metal or ammonium salt and preferably potassium formate. It may be used as an aqueous solution of any concentration but is preferably used when the molar water to formate ratio is the optimum for the desirable compound (for example moles $H_2O$/moles formate=3 for 2-nitrotoluene, nitrobenzene, 4-nitrophenetole etc.). The pH of the reduction medium may be adjusted as desired in order to achieve pH higher than 7. The preferably pH range is about 7 and about 9.

The theoretical usages of formic acid salts are two moles for an azo and triple bond containing compound, 3 moles for a nitro containing compound and one mole for a double bond group. Excellent results are obtained when those theoretical amounts are used but excess of the hydrogen donor will, of course, shorten the processes.

The hydrogen catalyst which can be used are preferably those based on Group VIII metals, but the best results are obtained with palladium on carbon.

The reaction is carried out conveniently at temperatures up to 200° C. Operating at atmospheric pressure, temperatures of 60°-130° C. are effective, but the temperatures range 70°-120° C. is preferred.

The process could be carried out in organic solvents that are water-insoluble such as toluene, benzene, xylene etc., however, the use of alcohols such as ethanol, propanol, isopropanol or butanol is preferred.

If desired the reaction may be carried out in the presence of an inert gas such as nitrogen. The products of this invention are useful for example, for the synthesis of amino aromatics as intermediates for the manufacture of dyestuffs and the synthesis of saturated compounds in the pharmaceutical industry.

This invention also provides a hydrogenation process and is especially useful for users far away from hydrogen sources that must store and transport hydrogen gas in pressurized cylinders.

Thus, hydrogen gas could also be obtained as such, by reacting the aqueous formate salt in the presence of a catalyst (Reaction 2)

$$HCO_2^- + H_2O \xrightarrow{cat} HCO_3^- + H_2 \quad (2)$$

as stated in the Israel specification No. 75580.

As stated the formic acid salt is preferably an alkali metal salt, but ammonium or trialkyl ammonium formate may also be used. It has also been found that adjusting the amounts of water present can be used to enhance the obtaining of high conversion and rates.

Thus the process is preferrably carried out wherein the water to formate molar ratio is about 0.5:1 to about 5:1 and especially preferred is a water to formate molar ratio of about 1:1 to about 3:1.

As shown in Table 1 hereinafter for the special case of 2-nitrotoluene as substrate the molar water to formate ratio can be optimized for the hydrogenation process and if the appropriate ratio is used the reduction process is performed at low temperatures at atmospheric pressures and in the absence of any surface active agent and/or phase transfer catalyst. As seen in Table 1 the optimal water to formate ratio on a molar basis is about 2.7.

The experiments tabulated in Table 1 were carried out with 50 mmol nitrotoluene 50 cc toluene, 150 mmol $KHCO_2$, 0.3 g pd/c(10%) and at a temperature of 70° C.

TABLE 1

| Water to formate Ratio influence on the Hydrogenation Rate of 2-Nitrotoluene | | | | | | | |
|---|---|---|---|---|---|---|---|
| Mole Water/Mol Formate | 0.06 | 1.0 | 2.0 | 2.66 | 3.33 | 5.0 | 6.66 |
| Initial M/min Rate | 0.015 | 0.03 | 0.09 | 0.13 | 0.09 | 0.064 | 0.035 |

As also can be seen from table 1 reactions may be performed in different water to formate ratios, but higher temperatures and/or longer times are required to reach complete conversion when low formate concentrations are used. Thus, e.g. British Pat. No. 1457608 uses in the examples therein water to formate ratios of about 5.5–11.5. In addition it discloses mainly the use of sodium formate as hydrogen donor. According to the present invention it has now been found that the nature of the hydrogen donor is also important. Potassium formate has shown higher activity in comparison to sodium formate regarding both rates and final conversion as can be seen from Table 2.

The experiments tabulated in Table 2 were carried out with 50 mmol nitrotoluene, 50 cc toluene, 150 mmol formate salt, 1000 mmol water 0.3 g pd/c (10%) and at a temperature of 70° C.

TABLE 2

| Hydrogenation of 2-Nitrotoluene by Formate Salts | | | | | | | |
|---|---|---|---|---|---|---|---|
| Time (min) | 5 | 10 | 30 | 50 | 60 | 120 | 180 |
| % conv. $KHCO_2$ | 10 | 45 | 80 | 88 | 92 | 99 | 100 |
| % conv. $NaHCO_2$ | 3 | 7 | 20 | 26 | 28 | 40 | 47 |

One of the reasons for such differences is the lower solubility of the resulting sodium bicarbonate (Reaction 1) that precipitates on the catalyst surface neutralizing its activity.

Those facts explain the essential presence of a surface active agent and/or a phase transfer catalyst in addition to the large excess of hydrogen donor at high temperatures in the processes disclosed in British Pat. Nos. 1457608 and 1458633. In addition, a better understanding of the reaction mechanism led to the present discovery of the important role that a preferred water to formate ratio plays in the process herein disclosed. Similarly use of an organic solvent and especially of an alcohol such as isopropanol, ethanol or butanol enhances the reaction rate. The mechanistic features of this process is outside of the scope of the present invention and will be published elsewhere in the future.

The bicarbonate resulting from the reaction may be recycled by means of formic acid to the formate salt avoiding the use of new formate salt in each new batch process reaction (Reaction 3). The resulting bicarbonate is partially transformed to carbonate (Reaction 4) depending on the temperatures applied in the process, but it also could be recycled as stated before by means of formic acid (Reaction 5).

$$MHCO_3 + HCOOH \rightarrow MHCO_2 + CO_2 + H_2O \quad (3)$$

$$2MHCO_3 \rightarrow M_2CO_3 + H_2O + CO_2 \quad (4)$$

$$M_2CO_3 + 2HCOOH \rightarrow 2MHCO_2 + CO_2 + H_2O \quad (5)$$

Recycling of the resulting bicarbonate/carbonate resulted in a net process in which formic acid is the $H_2$ donor (Reaction 6).

$$ArNO_2 + 3HCOOH \rightarrow ArNH_2 + 3CO_2 + 2H_2O \quad (6a)$$

$$R-HC=CH-R + HCOOH \rightarrow RCH_2-CH_2R- + CO_2 \quad (6b)$$

The formate salt may be produced by any of the processes known in the art (Reaction 6-8) or by hydrogenation of bicarbonate as disclosed in Israel Specification 75580 (Reaction 9).

$$MOH + HCOOH \rightarrow MHCO_2 + H_2O \quad (6)$$

$$MHCO_3 + HCOOH \rightarrow MHCO_2 + CO_2 \quad (7)$$

$$M_2CO_3 + 2HCOOH \rightarrow 2MHCO_2 + CO_2 + H_2O \quad (8)$$

$$MHCO_3 + H_2 \rightarrow MHCO_2 + H_2O \quad (9)$$

As stated before the bicarbonate/carbonate resulting from the reaction (reaction 1) can be recycled after reaction to formate by the addition of formic acid (reaction 3-5). Alternatively it is also possible to add formic acid to the basic solution of bicarbonate/carbonate/formate while the reaction is proceding, thus always maintaining a definite amount of bicarbonate/carbonate in solution. In this way the reaction may proceed with a fixed amount of formate/bicarbonate/carbonate and adding formic acid dropwise allows for the in situ generation of formate by reaction with carbonate and/or bicarbonate. It is preferred in this process to always maintain an excess amount of bicarbonate in order to maintain a basic pH.

The invention will now be described in connection with certain preferred embodiments with reference to the following illustrative examples so that it may be more fully understood. It is stressed, however, that the particulars described are by way of example and for purposes of illustrative discussion only and are presented in the cause of providing what is believed to be the most useful and readily understood description of the principles and conceptual aspects of the invention. Thus, the following examples which include preferred embodiment will serve to illustrate the practice of this invention, it being understood that the particulars described are by way of example and for purposes of illustrative discussion of preferred embodiments of the present invention only.

EXAMPLE 1

0.05 mol of 2-nitrotoluene are dissolved in 25 ml toluene and to this solution is added 0.3 grs of 10% Palladium on carbon (50% paste) and a solution containing 0.15 mol potassium formate and 0.400 mol of water. The mixture is stirred rapidly and heated to 70° C. After one hour of reaction the mixture is filtered and phase separated. The organic phase is washed with water (3×50 ml), the extract dried over $MgSO_4$ and the solvent is removed by distillation to give 0.045 mol of 2-aminotoluene (90% yield).

EXAMPLE 2

0.05 mol of 4-nitrophenetole are treated as in Example 1. Distillation of the product afforded 0.047 mol of 4-aminophenetole (94% yield).

EXAMPLE 3

0.05 mol of nitro benzene are treated as in example 1. Vacuum distillation of the solvent afforded 0.048 mol of the amino benzene (95% yield).

EXAMPLE 4

0.05 mol of 2-nitro toluene were treated as in example 1 but using 25 ml ethanol as solvent and 0.1 grs 10% Palladium on carbon (50% paste) as catalyst. After 20 minutes reaction the mixture was filtered and treated as stated in Example 1. Distillation of the product afforded 0.042 mol of 2-amino toluene (84% yield).

EXAMPLE 5

0.05 mol of styrene were dissolved in 20 mol toluene. To the mixture 0.2 grs of 10% Palladium on carbon were added, and then the mixture was heated at 70° C. 0.06 Mol of potassium formate and 0.1 mol $H_2O$ were then added. After 1 hour reaction, the conversion of ethylbenzene was 100% as examined by gas chromatographic analysis.

EXAMPLE 6

Use of Sodium Formate instead of Potassium Formate 0.05 mol of 2-Nitrotoluene in 25 ml toluene were stirred at 70° C. with 0.3 grs 10% Palladium on charcoal, 0.15 mol sodium formate and 0.4 mol of water. After 2 hrs the conversion of 2 amino toluene was 30% and remained unchanged after further heating as examined by gas chromatographic analysis. The 70% 2-nitroluene remain unchanged until a fresh quantity of the catalyst was added, indicating that the neutralization of the Palladium was responsible for the low conversion. After 2 hrs the conversion of 2 amino toluene was 60% and remains unchanged. 0.1 mol Formic acid were then added dropwise for 1 hr and afterwards the conversion was 95% as examined by gas chromatographic analysis.

EXAMPLE 7

0.05 Mol of 4 nitro ethyl benzoate were dissolved in 25 cc butanol, 0.01 grs of 10% Palladium on carbon were added and the mixture heated to reflux. 0.1 mol of potassium formate and 0.1 mol of $H_2O$ were then also added. After 30 minutes the conversion of 4 Amino Ethyl Benzoate was 30%. 0.06 mol of 98% Formic acid were then added dropwise during two hours. After all the formic acid was added the conversion was 100% as examined by gas chromatographic cnalysis.

COMPARATIVE EXAMPLE A

Use of a phase transfer catalyst 0.05 mol of 2 nitro toluene were treated as in Example 1 but 0.3 grs of trioctyl-methyl ammonium bromide (Aliquat 336). After 2 hrs the conversion of 2-aminotoluene was 33%, proving that under the process conditions disclosed in this invention, the use of a Phase Transfer Catalyst not only does not accelerate the reaction rate but lowers it.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A three phase method for reducing water insoluble organic compounds containing reducible nitro groups or reducible carbon-carbon unsaturated bonds comprising contacting an organic phase containing said water insoluble organic compounds which are to be reduced with an aqueous solution of a potassium formic acid salt which serves as hydrogen donor in the presence of a solid heterogeneous palladium on carbon hydrogenation catalyst and in the absolute absence of a phase transfer catalyst or any surface active agent, wherein the water to formate molar ratio is about 0.5:1 to about 3:1 and the pH is greater than 7.

2. A process according to claim 1 wherein the water to formate molar ratio is about 1:1 to about 3:1.

3. A process according to claim 1 wherein said process is carried out at a temperature up to about 200° C.

4. A process according to claim 3 carried out at temperatures of about 60°–130° C.

5. A process according to claim 1 wherein said organic compound is a water immiscible or sparingly water soluble aromatic or heteroaromatic compound containing a nitro group.

6. A process according to claim 1 wherein said organic compound is a water immiscible or sparingly water soluble carbon-carbon unsaturated compound.

7. A process according to claim 1 wherein said process is carried out in an organic solvent which is substantially inert in the reaction conditions.

8. A process according to claim 7 wherein said solvent is an alcohol.

9. A process according to claim 1 wherein formic acid is periodically added to the reaction medium during the course of the reaction.

10. A process according to claim 9 wherein said medium is maintained with an excess amount of bicarbonate in order to maintain a basic pH.

* * * * *